(12) United States Patent
Kalava et al.

(10) Patent No.: US 10,231,799 B1
(45) Date of Patent: Mar. 19, 2019

(54) OVERHEAD LIGHT SHIELD

(71) Applicants: Arun Kalava, Tampa, FL (US);
Nataliya Grygoryeva, Tampa, FL (US)

(72) Inventors: Arun Kalava, Tampa, FL (US);
Nataliya Grygoryeva, Tampa, FL (US)

( * ) Notice: Subject to any disclaimer, the term of this patent is extended or adjusted under 35 U.S.C. 154(b) by 0 days.

(21) Appl. No.: 15/830,827

(22) Filed: Dec. 4, 2017

Related U.S. Application Data

(60) Provisional application No. 62/429,954, filed on Dec. 5, 2016.

(51) Int. Cl.
| | | |
|---|---|---|
| *F21V 3/00* | (2015.01) | |
| *F21V 5/00* | (2018.01) | |
| *A61B 90/30* | (2016.01) | |
| *F21V 21/40* | (2006.01) | |
| *F21V 17/10* | (2006.01) | |
| *F21V 3/04* | (2018.01) | |
| *F21W 131/205* | (2006.01) | |

(52) U.S. Cl.
CPC ............. *A61B 90/30* (2016.02); *F21V 3/04* (2013.01); *F21V 17/101* (2013.01); *F21V 21/403* (2013.01); *F21W 2131/205* (2013.01)

(58) Field of Classification Search
CPC ...... Y10S 362/804; F21S 41/20; F21S 41/285
USPC .................................... 362/311.01, 400, 804
See application file for complete search history.

(56) References Cited

U.S. PATENT DOCUMENTS

| | | |
|---|---|---|
| 4,559,671 A | 12/1985 | Andrews |
| 4,605,124 A | 8/1986 | Sandel et al. |
| 5,142,736 A | 9/1992 | Kuebn et al. |
| 5,355,292 A | 10/1994 | Hoftman et al. |
| 5,599,093 A | 2/1997 | Hoftman et al. |
| 5,709,465 A | 1/1998 | Lanzone |
| 6,129,208 A | 10/2000 | Ferguson |
| 6,155,695 A | 12/2000 | Sealy |
| 6,692,141 B2 | 2/2004 | Jesurun et al. |
| 6,878,425 B1 | 4/2005 | Gomes |
| D568,528 S | 5/2008 | Hood |
| 7,389,869 B2 | 6/2008 | Mason |
| 8,940,122 B2 | 1/2015 | Cohen et al. |
| D729,973 S | 5/2015 | Gebhard et al. |
| 2011/0267793 A1 | 11/2011 | Cohen et al. |
| 2013/0098549 A1 | 4/2013 | Drage et al. |

*Primary Examiner* — Daniel St Cyr
(74) *Attorney, Agent, or Firm* — Frijouf, Rust & Pyle, P.A.

(57) ABSTRACT

An overhead light shield is disclosed including a first and a second optically transparent film being partially circle. The first and second optically transparent film includes a notch. The first and second optically transparent films have an upper film side and a lower film side wherein the lower film side has an adhesive layer. The first and second optically transparent films include a plurality of film tabs extending outwardly from the optically transparent circumferential edges. The optically transparent films are protected by a first and a second peel-away film that is removably affixed. The peel-away films contain tabs extending outwardly from the first peel-away film circumferential edges. The optically transparent film tabs and the peel-away film tabs define grasping tabs for positioning the optically transparent film to the surgical room light. The optically transparent film adhesive layers couple the optically transparent films to the surgical room light.

22 Claims, 10 Drawing Sheets

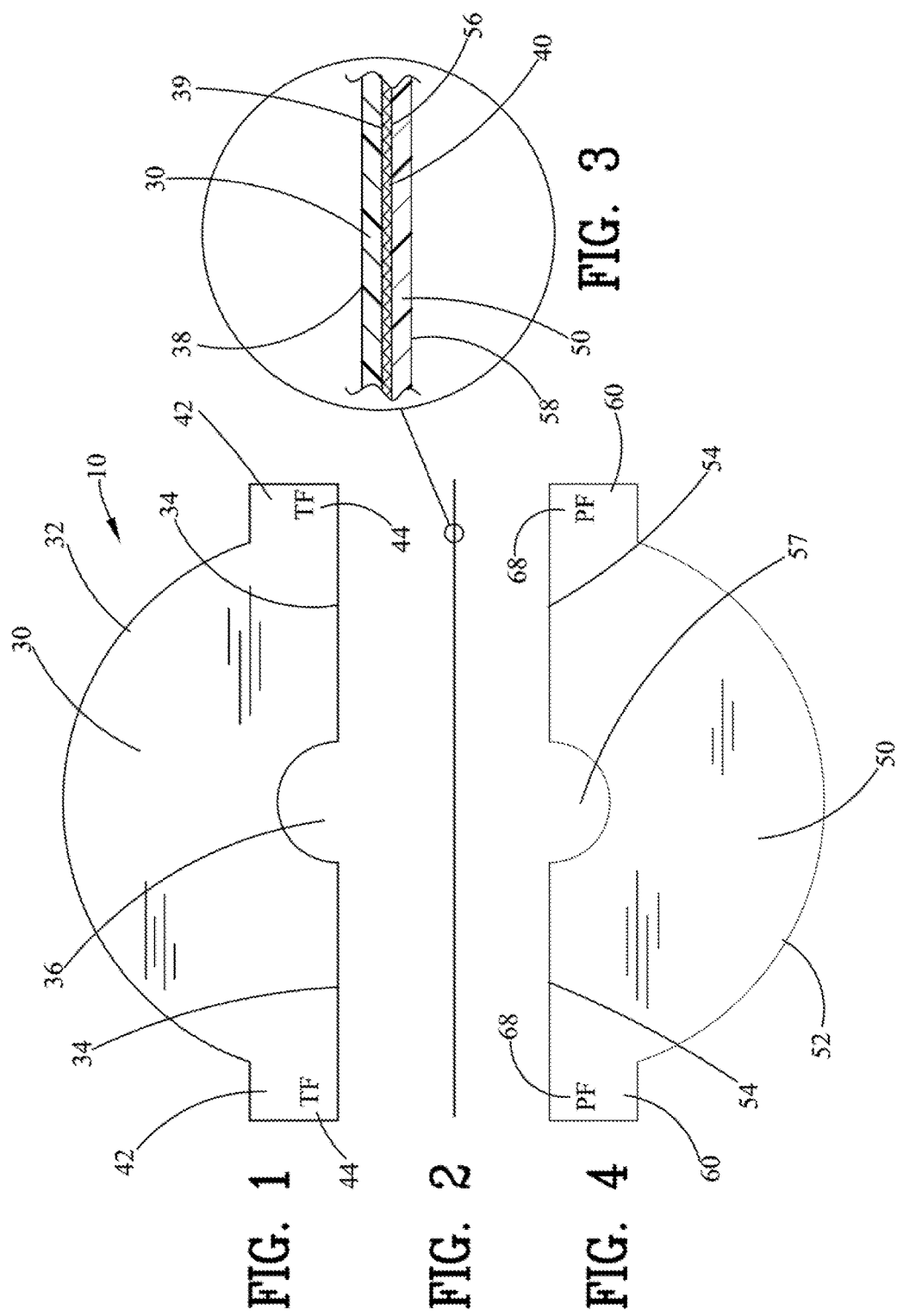

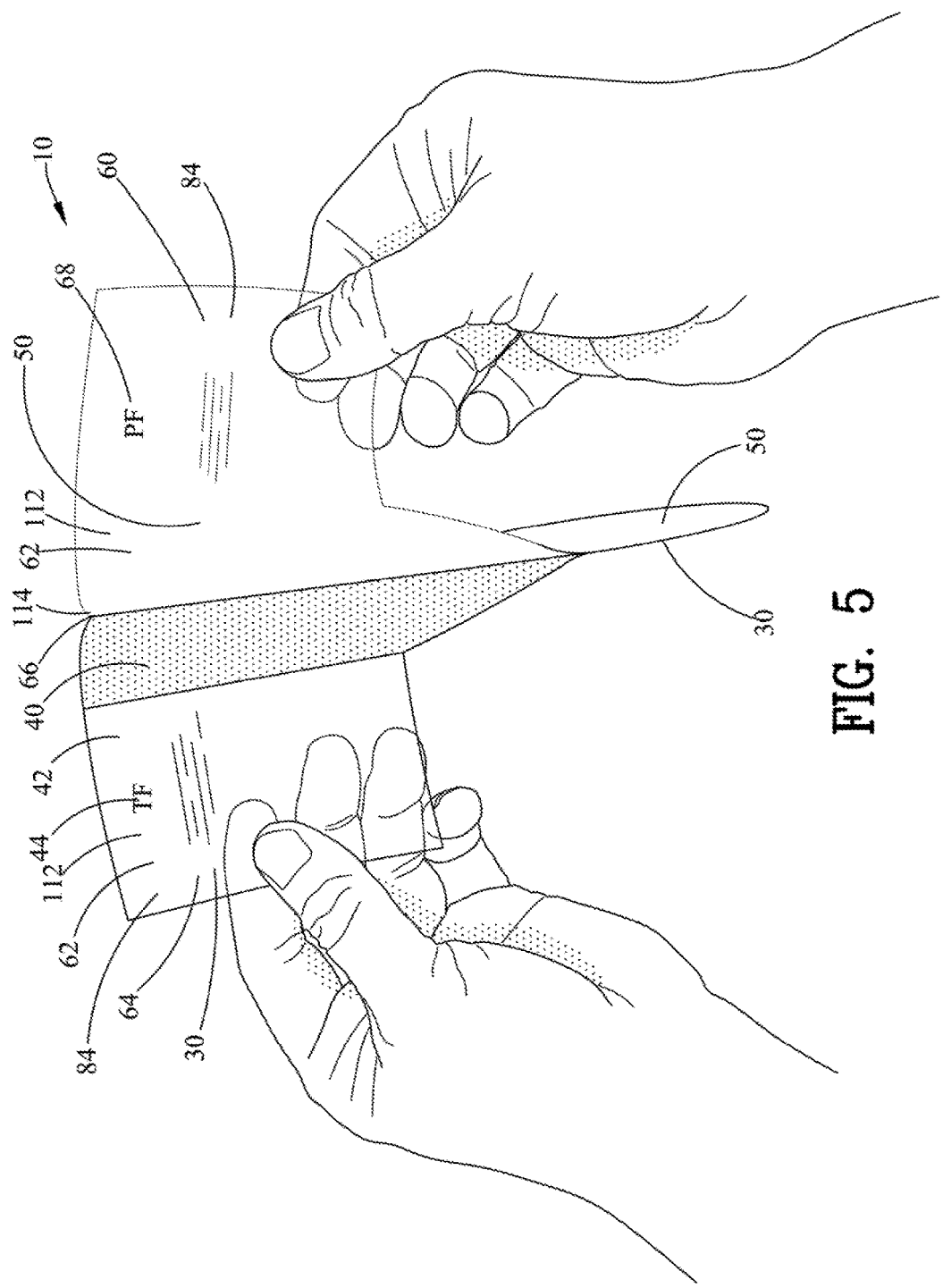

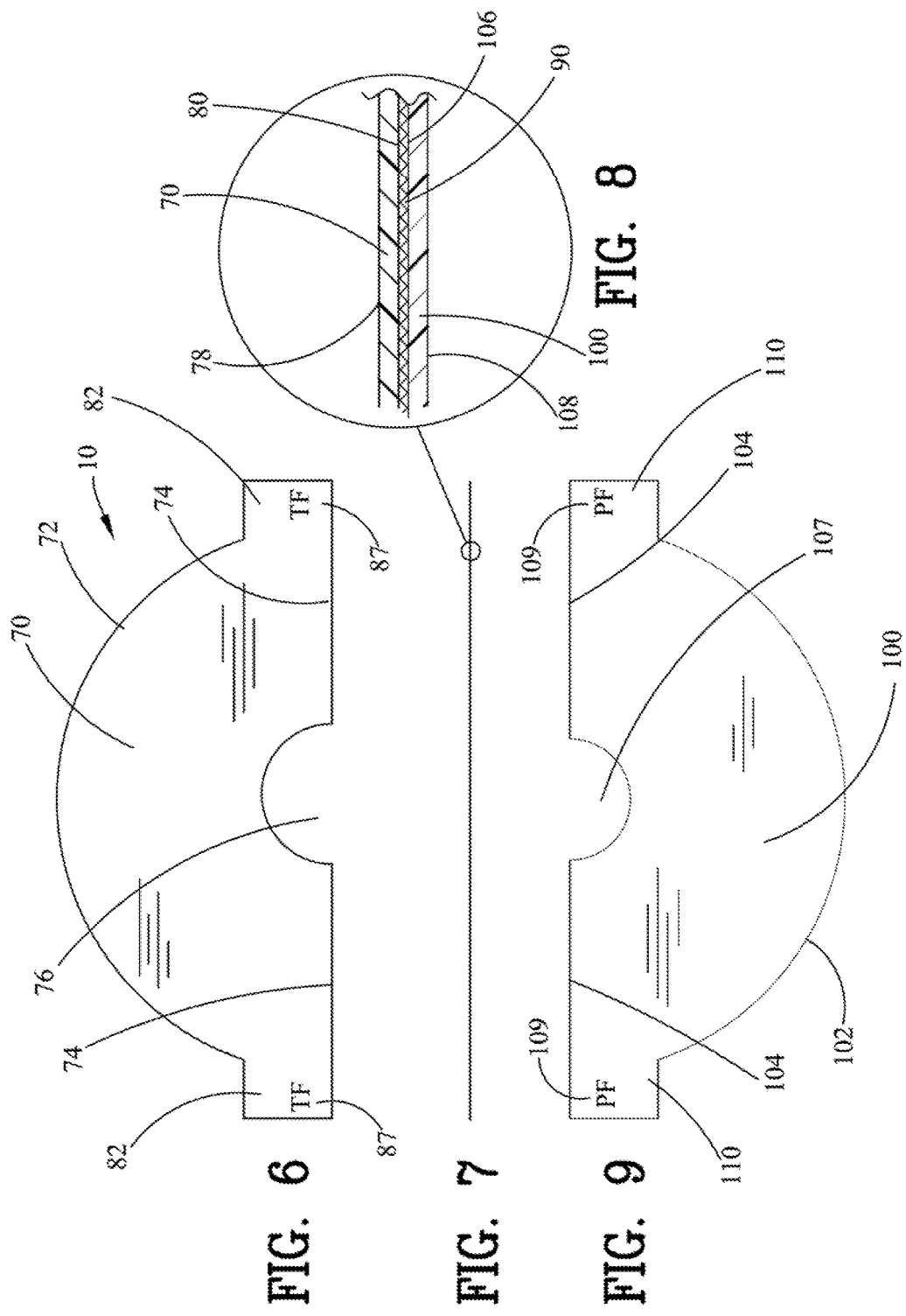

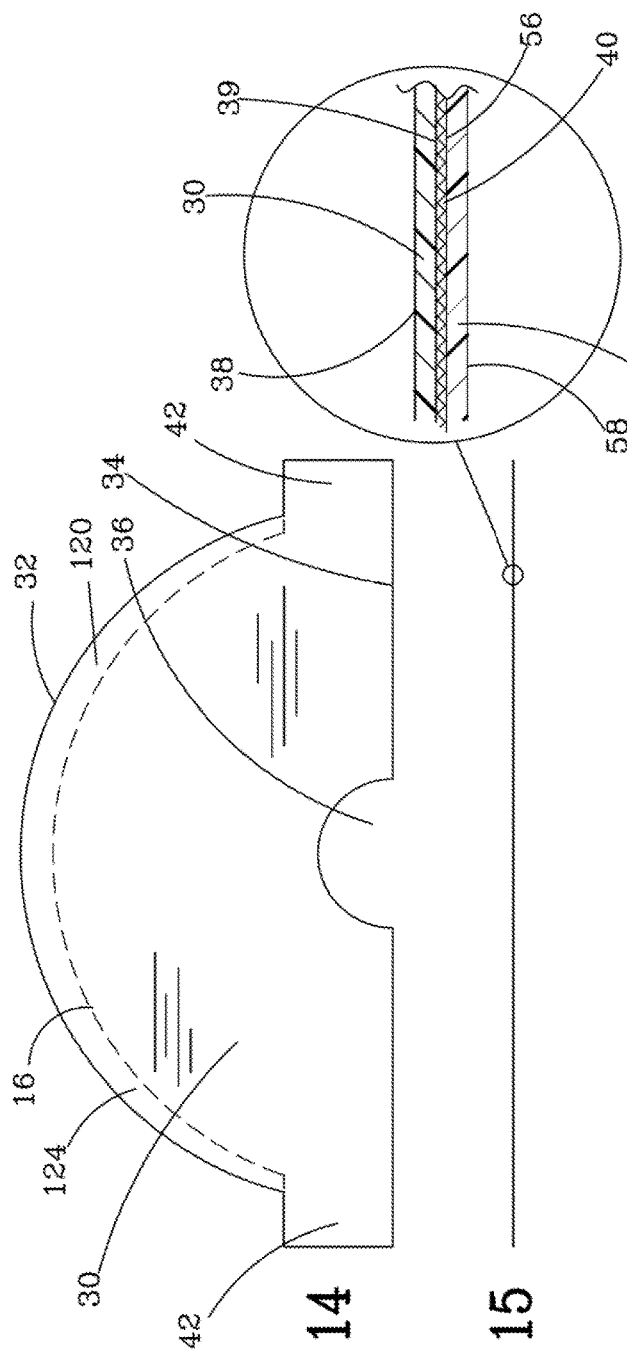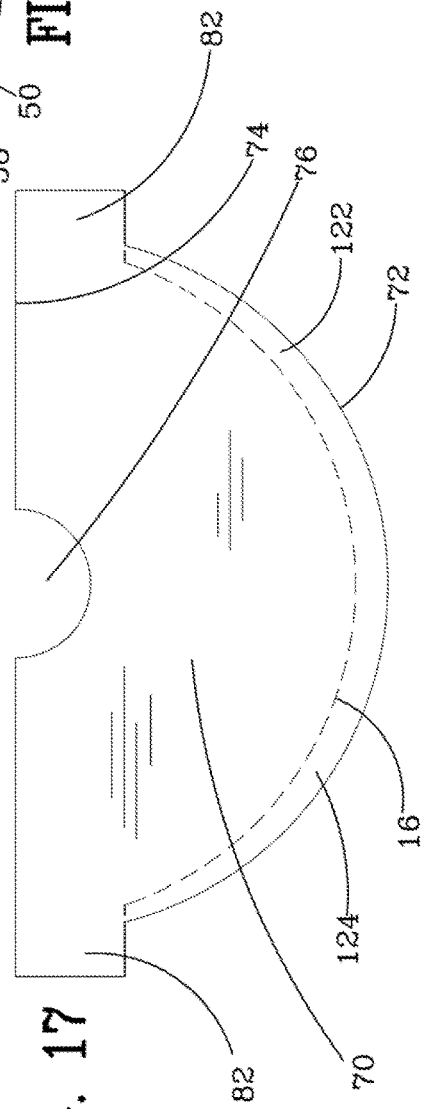

OVERHEAD LIGHT SHIELD

CROSS-REFERENCE TO RELATED APPLICATIONS

This application claims benefit of U.S. Patent Provisional application No. 62/429,954 filed Dec. 5, 2016. All subject matter set forth in provisional application No. 62/429,954 is hereby incorporated by reference into the present application as if fully set forth herein.

BACKGROUND OF THE INVENTION

Field of the Invention

This invention relates to a light cover and more particularly to a light cover for a surgical light.

Description of the Related Art

The need to help others, especially family, has been instilled on humans from the Neolithic and pre-Classical ages, however, many never survived. Just over a hundred years ago, it was found that microorganisms during the surgery were partially to blame for the cause of death. It was then recommended that the use of carbolic acid as a sterilizing agent to remove the microorganisms from the wounds, all surgical instruments and even the air around the patient should be practiced. The sterilizing practice was cumbersome and therefore not widely practiced. Today however, the use of less cumbersome methods such as autoclaves and chemical antiseptics to sterile the operating room environment lead some doctors believe that a sterile environment has been achieved.

Doctors are continually performing more and more precise operations and high emitting operating room lights are required for the doctors to see in more detail. Operating room lights tend to be positioned above the patient during surgery and therefore imperative that the lights be sterile during the intra-operative period. The operating room lights cannot fit, nor are recommended to be cleaned with an autoclave, so a person must manually wipe down the operating room lights with chemical antiseptics, sometimes hours before the operation. The time from when the operating room lights are sterilized to operation allows the operating room lights to become unsterile, or an imperfect cleaning of the operating room lights can allow microorganisms to remain on the operating room lights. The microorganisms on an operating room lightshave high probability of landing on the patient and into the surgical wound causing infections during the times the operating room light is positioned above the patient. The majority of times, doctors need to position the operating room lights above the patient during operation which put the patient at risk of infections from falling microorganisms.

There have been many in the prior art who have attempted to solve these problems with varying degrees of success. None, however completely satisfies the requirements for a complete solution to the aforestated problem. The following U.S. Patents are attempts of the prior art to solve this problem.

U.S. Pat. No. 4,559,671 to Andrews et. discloses a sterile handle cover is disclosed for covering a lamp handle of a surgical lamp to provide a sterile surface for adjustment of the lamp by an operator. The handle cover comprises a grip portion defined by a first and a second end. An end wall is integrally attached proximate the first end of the grip portion to form a hollow container open at the second end. A protector is connected to the second end of the grip portion and extends radially outwardly for protecting the hand of the operator from contacting portions of the surgical lamp proximate the lamp handle. A plurality of ribs are disposed in the grip portion for frictionally engaging the lamp handle of the surgical lamp to maintain the position of the handle cover thereon.

U.S. Pat. No. 4,605,124 to Sandel et. discloses a sterile cover for the handle on a surgical light is comprised of an integrally formed disposable plastic sheath generally in the shape of a unibody hollow cylinder with either a hollow inverse conical-shaped member or a dish shaped member at an open end of the cylinder. An alternative embodiment of the invention relates to an adapter kit having an adapter bushing, an adapter handle for threaded or snap-on attachment to the stud on any of a variety of lighting fixtures and sterile covers to allow the covers to be used on light fixtures having different sizes of handle mounting studs.

U.S. Pat. No. 5,142,736 to Kuehn et. discloses a protective sleeve for covering the handles of a dentist's light is formed of two flexible plastic panels joined at four edges and having an aperture cut therein to allow access to the interior of the sleeve. The T-shaped handle of the light is inserted into the aperture, which is preferably elliptical in shape, and the sleeve pulled onto the handle. The sleeve is pulled off the handle after completion of a procedure on a patient and a new sleeve is put on before treatment of the next patient, thus avoiding possible transmission of disease from one patient to another from contact with the light handle.

U.S. Pat. No. 5,355,292 to Hoftman et. discloses an assembly for attachment to a conventional operating room light fixture includes a handle and a disposable cover. The handle has an upper portion adapted to be attached to the light fixture. The handle further includes an annular rigid disk at a central portion thereof and an annular ring provided below the annular rigid handle flange and defining a groove therebetween. A grip portion is provided at a lower portion of the handle. The assembly also includes a sterile, disposable cover, including a hollow grip cover having a closed end and a flexible flange formed integrally with the grip cover at an open end thereof and adapted to be fitted over the grip portion of the handle and advanced thereon. The disposable cover further includes a circular rigid cover flange attached to the flexible flange and curved away from the rigid disk when the grip cover is fitted over the grip portion of the handle, with the rigid disk restraining further advancement of the rigid cover flange. The rigid cover flange also includes an opening corresponding to the open end of the grip cover, and a plurality of snaps provided along the circumference of the opening and adapted to be fitted within the groove to securely fit the disposable cover over the handle. For industry-standard handles available with some operating room light fixture, a light handle adapter may be attached to the standard handle to secure the disposable cover onto the handle. The light handle adapter is slid up the handle toward the light fixture. The light handle adapter may be affixed to the light handle by an adhesive or other mechanical means, and the disposable cover is secured to the light handle adapter.

U.S. Pat. No. 5,599,093 to Hoftman et. discloses an assembly for attachment to a conventional operating room light fixture includes a handle and a disposable cover. The handle has an upper portion adapted to be attached to the light fixture. The handle further includes an annular rigid disk at a central portion thereof and an annular ring provided below the annular rigid handle flange and defining a groove therebetween. A grip portion is provided at a lower portion of the handle. The assembly also includes a sterile, disposable cover, including a hollow grip cover having a closed end and a flexible flange formed integrally with the grip cover at an open end thereof and adapted to be fitted over the grip portion of the handle and advanced thereon. The disposable cover further includes a circular rigid cover flange attached to the flexible flange and curved away from the rigid disk when the grip cover is fitted over the grip portion of the handle, with the rigid disk restraining further advancement of the rigid cover flange. The rigid cover flange also includes an opening corresponding to the open end of the grip cover, and a plurality of snaps provided along the circumference of the opening and adapted to be fitted within the groove to securely fit the disposable cover over the handle. For industry-standard handles available with some operating room light fixtures, a light handle adapter may be attached to the standard handle to secure the disposable cover onto the handle. The light handle adapter is slid up the handle toward the light fixture. The light handle adapter may be affixed to the light handle by an adhesive or other mechanical means, and the disposable cover is secured to the light handle adapter.

U.S. Pat. No. 5,709,465 to Lanzone discloses a disposable cover for a handle of a fixture which is nominally positioned within a sterile field comprises first and second panels formed of flexible, medical grade plastic film material bonded together at portions of their respective perimeters to form a receptacle including an open cuff merging with a hollow sleeve which is closed except at the cuff and is shaped and dimensioned to receive a grip portion of the handle.

U.S. Pat. No. 6,129,208 to Ferguson discloses a plant flat-collapsible-container made from a first panel of thin heat-sealable film, a second panel of thin heat-sealable film, a first decorative panel and a second decorative panel. The first panel, second panel, first decorative panel and second decorative panel are joined together along a first longitudinally-extending seam and a second longitudinally extending seam. The first longitudinally-extending seam forms a first angle with a transverse axis of the container. The second longitudinally-extending seam forms a second angle with a line drawn transverse to the axis of the container. The first and second angles can be the same, or, alternatively, the first angle can be between 55° and 65° and the second angle can be between 85° and 90°. The container can include a protruding portion which extends beyond a transversely-extending edge of the container. The protruding portion can have perforations.

U.S. Pat. No. 6,155,695 to Sealy discloses a light cover is provided for direct attachment to a light bulb of a decorative light. The light cover is made of a flexible material which is dyed to a desired color. The light cover because of its flexible material is adaptable for use with different sized light bulbs. The light cover does not substantially change the diffusion of the light projected, but achieves a desired color change. In a first embodiment, the light cover is cylindrical in shape with an integral cone-shaped cap. In a second embodiment, the cap is eliminated and the light cover is simply cylindrical in shape. The invention in one aspect is a light cover. In another aspect, the invention is a light cover in combination with a standard decorative light. In another aspect, the invention is an artificial Christmas tree of the type having improved decorative lighting.

U.S. Pat. No. 6,692,141 to Jesurun et. discloses an interface apparatus provides a sterile barrier between a sterile field and non-sterile portions of an associated surgical lighthead. The interface apparatus is a sterile disposable cover including a lower grippable portion, an intermediate cone-shaped portion, and an upper window area. The lower grippable portion is adapted to connect onto the handle portion of an associated surgical lighthead. An intermediate cone-shaped portion connects the lower grippable portion with an upper window area. The upper window area overlays control input means of the associated surgical lighthead such as, for example, light intensity controls. At least a portion of the upper window area is transparent to enable visualization of the control inputs beneath the sterile disposable cover. The interface apparatus is of a unitary or composite construction.

U.S. Pat. No. 6,878,425 to Gomes discloses a polarized filter film having a plurality of light-filtering layers each having a different polarization aperture and tint hue that can be selectively combined to form a polarized filter film having a combined opacity rating of 5% to 55% when applied to a transparent medium such as a window. The combined polarized filter film is comprised of a plurality of layers of light-filtering material wherein each layer has a plurality of apertures positioned either vertically or angularly so that the horizontal rays associated with glare are reduced dramatically. Each layer of film has a plurality of slotted apertures that is biased or offset from the overlaying light-filtering film apertures whereby varying degrees of light-blocking properties can be achieved by using the light-filtering films in conjunction with additional layers. The present invention is attached to the transparent medium by using an adhesive which has a removable protective backing layer.

U.S. Pat. No. 7,389,869 to Mason Jr. discloses a kit apparatus has a molded support card holding a plurality of film sheets each having an adhesive layer on one side, a spray bottle containing a cleaning and activating solution enabled for activating the adhesive layers of the film sheets, and a squeegee. The film sheets are secured within a first pocket in the support card, the squeegee secured within a second pocket in the support card, and the spray bottle is secured within a recess in the support card. Plural tabs extend over the recess for holding the spray bottle securely within the recess.

U.S. Pat. No. 8,940,122 to Cohen et discloses a protective adhesive film may include a polyurethane sheet and an adhesive layer disposed on at least a portion of a first major surface of the polyurethane sheet. The adhesive layer may comprise a pressure-sensitive adhesive that includes an acrylate polymer and a silicone macromer. The adhesive layer may adhere to a surface of an electronic device without the application of any liquid or additive to the adhesive layer or the surface of the electronic device.

U.S. Pat. D568,528 to Hood discloses the ornamental design for a clear plastic surgical light cover, as shown and described.

U.S. Pat. D729,973 to Gebhard et al discloses an ornamental design for an LED work light, as shown and described.

United States Patent 2011/0267793 to Cohen et. discloses a protective adhesive film may include a polyurethane sheet and an adhesive layer disposed on at least a portion of a first major surface of the polyurethane sheet. The adhesive layer may comprise a pressure-sensitive adhesive that includes an acrylate polymer and a silicone macromer. The adhesive layer may adhere to a surface of an electronic device without the application of any liquid or additive to the adhesive layer or the surface of the electronic device.

United States Patent 2013/0098549 to Drage et. al discloses a protective film that can be applied using a wet or dry application process. The protective film may be part of a protective film application kit that also includes a package and, optionally, liquid, installation tabs, and a squeegee.

Although the aforementioned prior art have contributed to the development of the art of an overhead light shield, none of these prior art patents have solved the needs of this art.

Therefore, it is an object of the present invention to provide an overhead light shield that prevents microorganisms from dropping from the operating room light while positioned above the patient and landing on the patient and into the surgical wound causing infections.

Another object of this invention is to reduce the time to prepare the operating room for surgery.

Another object of the present invention to provide an overhead light shield that is easy to install.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention within the scope of the invention. Accordingly other objects in a full understanding of the invention may be had by referring to the summary of the invention and the detailed description describing the preferred embodiment of the invention.

SUMMARY OF THE INVENTION

A specific embodiment of the present invention is shown in the attached drawings. For the purpose of summarizing the invention, the invention relates to an overhead light shield for covering a surgical room light wherein the surgical room light has a light surface, a circumferential edge and a center handle, the center handle having a handle circumferential edge, overhead light shield comprising a first optically transparent film being partially circle defining a first film circumferential edge and a first film edge. The first optically transparent film having a partial circular notch in the first optically transparent film interposed in the first film edge. The first optically transparent film having a first upper film side and a first lower film side. A first adhesive layer affixed to the first lower film side. A plurality of first film tabs affixed to and extending outwardly from the first film circumferential edge. A first peel-away film being partially circle defining a first peel-away film circumferential edge and a first peel-away film edge. The first peel-away film has a first upper peel-away film side and a first lower peel-away film side. The first upper peel-away film side is removably affixed to the first adhesive layer for protecting the first adhesive layer now located between the first optically transparent film and the first peel-away film. A plurality of first peel-away tabs being affixed to and extending outwardly from the first peel-away film circumferential edge. The plurality of first peel-away tabs and the plurality of first film tabs create a plurality of first disjoining tabs for separating the first peel-away film from the first adhesive layer. The plurality of first film tabs creates grasping tabs for holding and positioning the first optically transparent film to the surgical room light. The first adhesive layer creates a first coupling joint for bonding the first optically transparent film to the surgical room light.

A second optically transparent film being partially circle defining a second film circumferential edge and a second film edge. The second optically transparent film has partial circular notch interposed in the second film edge. The second optically transparent film has an upper film side and a lower film side wherein the lower film side has an adhesive layer affixed. A plurality of second film tabs being affixed to and extending outwardly from the second film circumferential edge. A second peel-away film being partially circle having a second circumferential edge and a second peel-away film edge. The second peel-away film has an upper peel-away film side and a lower peel-away film side. The second upper peel-away film side removably affixed to the second adhesive layer for protecting the second adhesive layer between the second optically transparent film and the second peel-away film. A plurality of second peel-away tabs being affixed to and extending outwardly from the second peel-away film circumferential edge. The plurality of second peel-away tabs and the plurality of second film tabs defining a plurality of second disjoining tabs for separating the second peel-away film from the second adhesive layer. The plurality of second film tabs defining a plurality of second grasping tabs for positioning the second optically transparent film to the surgical room light. The second adhesive layer creates a coupling joint for bonding the second optically transparent film to the surgical room light.

In a more specific embodiment of the invention, the overhead light shield the first film circumferential edge extends beyond the surgical room light circumferential edge for defining a first cantilever film portion and the second film circumferential edge also extends beyond the surgical room light circumferential edge for defining a second cantilever film portion. The first cantilever film portion and the second cantilever film portion create an exterior annular ring for trapping microorganisms descending from above the light surface.

In an another embodiment of the invention, the first film edge and the second film edge abutting for defining a contiguous joint for covering the light surface.

In an another embodiment of the invention, the first film edge and the second film edge abutting for defining a contiguous joint for covering the light surface.

In an another embodiment of the invention, the first partial circular notch and the handle circumferential edge abutting for creating a first contiguous abutment and the second partial circular notch and the handle circumferential edge abutting for creating a second contiguous abuttment.

The foregoing has outlined rather broadly the more pertinent and important features of the present invention in order that the detailed description that follows may be better understood so that the present contribution to the art can be more fully appreciated. Additional features of the invention will be described hereinafter which form the subject matter of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which:

FIG. 1 is a view of the first optically transparent film for the first embodiment for an overhead light shield incorporating the present invention;

FIG. 2 is a side view of the overhead light shield including the first optically transparent film and the first peel-away film;

FIG. 3 is an enlarged portion of FIG. 2 showing first optically transparent film, the first peel-away film and the first adhesive layer;

FIG. 4 is a view of the first peel-away film for the first embodiment for an overhead light shield incorporating the present invention;

FIG. 5 is a view illustrating the separation of the first optically transparent film from the first peel-away film;

FIG. 6 is a view of the second optically transparent film for the first embodiment for an overhead light shield incorporating the present invention;

FIG. 7 is a side view of the overhead light shield including the second optically transparent film and the second peel-away film;

FIG. 8 is an enlarged portion of FIG. 7 showing second optically transparent film, the second peel-away film and the second adhesive layer;

FIG. 9 is a view of the second peel-away film for the first embodiment for an overhead light shield incorporating the present invention;

FIG. 14 is a view showing the first optically transparent film circumferential edge extended so that the first optically transparent film circumferential edge will extend beyond the surgical room light circumferential edge;

FIG. 15 is a side view of FIG. 14;

FIG. 16 is an enlarged portion of FIG. 15 showing first optically transparent film, the first peel-away film and the first adhesive layer;

FIG. 17 is a view showing the second optically transparent film where the second optically transparent film circumferential edge extended so that the first optically transparent film circumferential edge will extend beyond the surgical room light circumferential edge;

Similar reference characters refer to similar parts throughout the several Figures of the drawings.

DETAILED DISCUSSION

Figure 10:
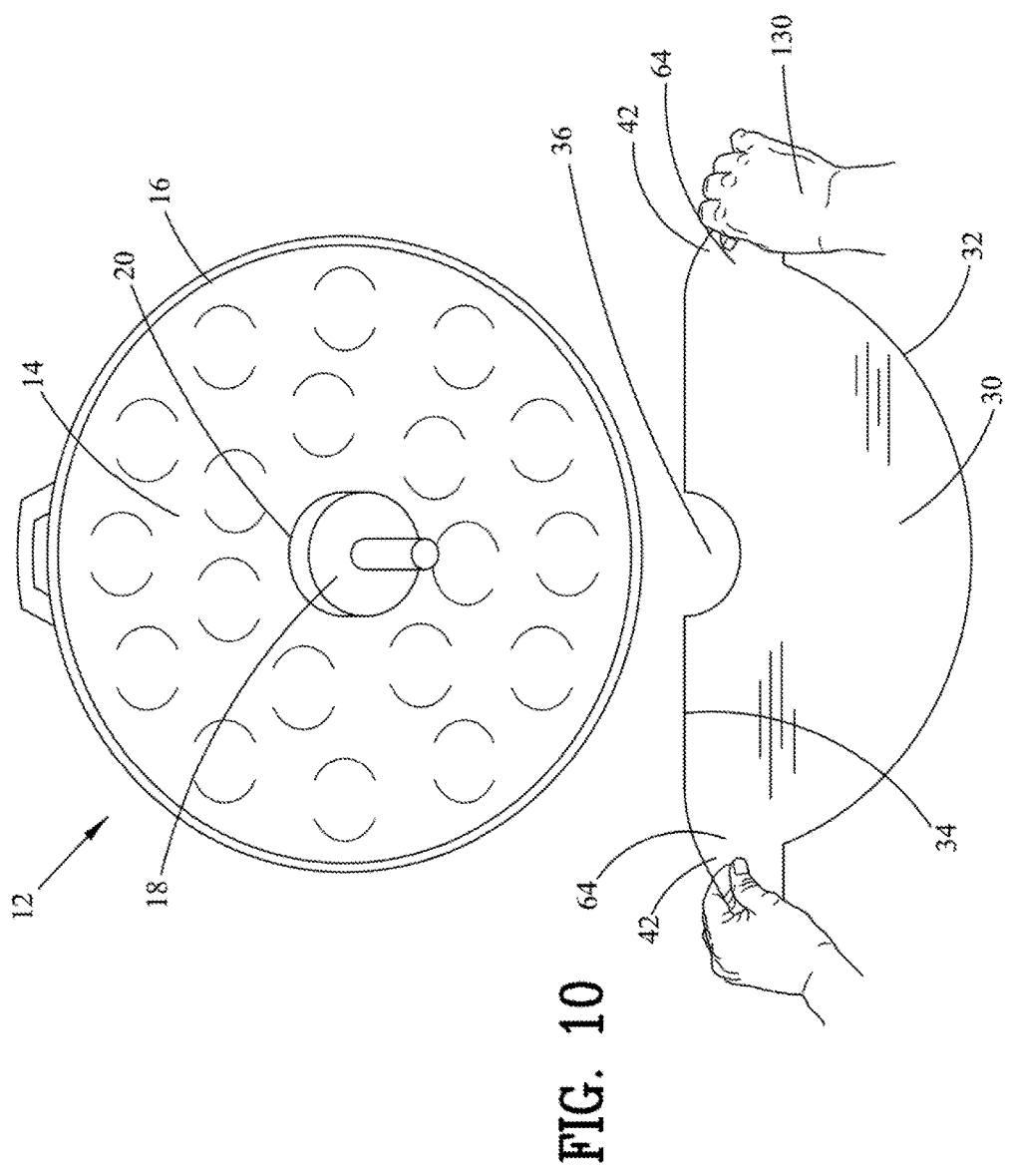
FIG. 10 is a view of a surgical light and illustrating the placement of the first optically transparent film to the surgical room light.

FIGS. 1-19 illustrate an overhead light shield 10 for covering a surgical room light 12. The surgical room light 12 has a light surface 14, a circumferential edge 16 and a center handle 18. The center handle 18 has a handle circumferential edge 20. FIG. 1 shows a first optically transparent film 30 being partially circle having a first film circumferential edge 32 for allowing the first optically transparent film 30 to parallel the perimeter of the surgical room light circumferential edge 16. FIG. 1 further shows the first optically transparent film 30 having a first film edge 34. The first film edge 34, when installed, would be abutting with a diameter line of the light surface 14. A first partial circular notch 36 defined in the first optically transparent film 30 is interposed in the first film edge 34. The first partial circular notch 36 creates a void within the optically transparent film 30 for the surgical room light center handle 18.

FIG. 2 is a side view of the overhead light shield 10. FIG. 3 shows the side view of the overhead light shield 10 by enlarging a section of FIG. 2. FIG. 3 shows the overhead light shield 10 having a first optically transparent film 30, a first upper film side 38, a first lower film side 39 and the first adhesive layer 40. The first adhesive layer 40 is affixed to the first lower film side 39. FIG. 3 also shows the first peel-away film 50 having a first upper peel-away film side 56 and a first lower peel-away film side 58. The first upper peel-away film side 56 is removably affixed to the first adhesive layer 40 for protecting the first adhesive layer 40 between the first optically transparent film 30 and the first peel-away film 50. The first peel-away film 50 may be a thinner film than the first optically transparent film 30 for easier identification.

FIG. 1 and FIG. 5 show a plurality of first film tabs 42 that are affixed to and extending outwardly from the first film circumferential edge 32. The first film tabs 42 may have a first film tabs symbol 44 for identifying the first optically transparent film 30. Shown in FIG. 4, is the first peel-away film 50 which is partially circle and defining a first peel-away film circumferential edge 52 and a first peel-away film edge 54. The first peel-away film 50 contains a plurality of first peel-away tabs 60 affixed to and extending outwardly from the first peel-away film circumferential edge 52. The first peel-away film tabs 60 may have a first peel-away film tabs symbol 68 for identifying the first peel-away film 50. FIG. 5 shows the plurality of first film tabs 42 and first peel-away tabs 60 defining a plurality of first disjoining tabs 62 for separating the first adhesive layer 40 from the first peel-away film 50. The plurality of first film tabs 42 define a plurality of first grasping tabs 64 for positioning the first optically transparent film 30 adjacent to the surgical room light 12. The first adhesive layer 40 defines a first coupling joint 66 for bonding the first optically transparent film 30 with the surgical room light 12. FIGS. 6, 7, 8 and 9 are similar to FIGS. 1, 2, 3, and 4 respectively.

FIGS. 6-9 show the second film and the second peel-away film. FIG. 6 shows a second optically transparent film 70 being partially circle defining a second film circumferential edge 72 and a second film edge 74. A second partial circular notch 76 defined in the second optically transparent film 70 is interposed in the second film edge 74. A plurality of second film tabs 82 are affixed to and extend outwardly from the second film circumferential edge 72. FIG. 6 also shows the second film tabs 82 having a second film tabs symbol 87 for identifying the second optically transparent film 70. FIG. 7 is a side view of the overhead light shield 10.

FIG. 8 shows the side view of the overhead light shield 10 by enlarging a section of FIG. 7. FIG. 8 shows the second optically transparent film 70 having a second upper film side 78 and a first lower film side 80 and the second adhesive layer 90 being affixed to the first lower film side 80. FIG. 8 also shows the second peel-away film 100 having a first upper peel-away film side 106 and a first lower peel-away film side 108. The second upper peel-away film side 106 is removably affixed to the second adhesive layer 90 for protecting the second adhesive layer 90 between the second optically transparent film 70 and the second peel-away film 100. The second peel-away film 100 may be a thinner film than the first optically transparent film 70 for easier identification.

FIG. 9 shows a second peel-away film 100 being partially circle defining a second peel-away film circumferential edge 102 and a second peel-away film edge 104. A plurality of second peel-away tabs 110 is affixed to and extending outwardly from the second peel-away film circumferential edge 102. The plurality of second peel-away tabs 110 and the plurality of second film tabs 82 define a plurality of second disjoining tabs 112, best shown in FIG. 5, for separating the second peel-away film 100 from the second adhesive layer 90. The plurality of second film tabs 82, best shown in FIG. 6, defines a plurality of second grasping tabs 84, best shown in FIG. 5, for positioning the second optically transparent film 70 adjacent to the surgical room light 12. The second adhesive layer 90, best shown in FIG. 8, defines a second coupling joint 114, best shown in FIG. 5, for bonding the second optically transparent film 70 with the surgical room light 12. The second peel-away film tabs 110 may have a second peel-away film tabs symbol 109 for identifying the second peel-away film 100.

Figure 11:
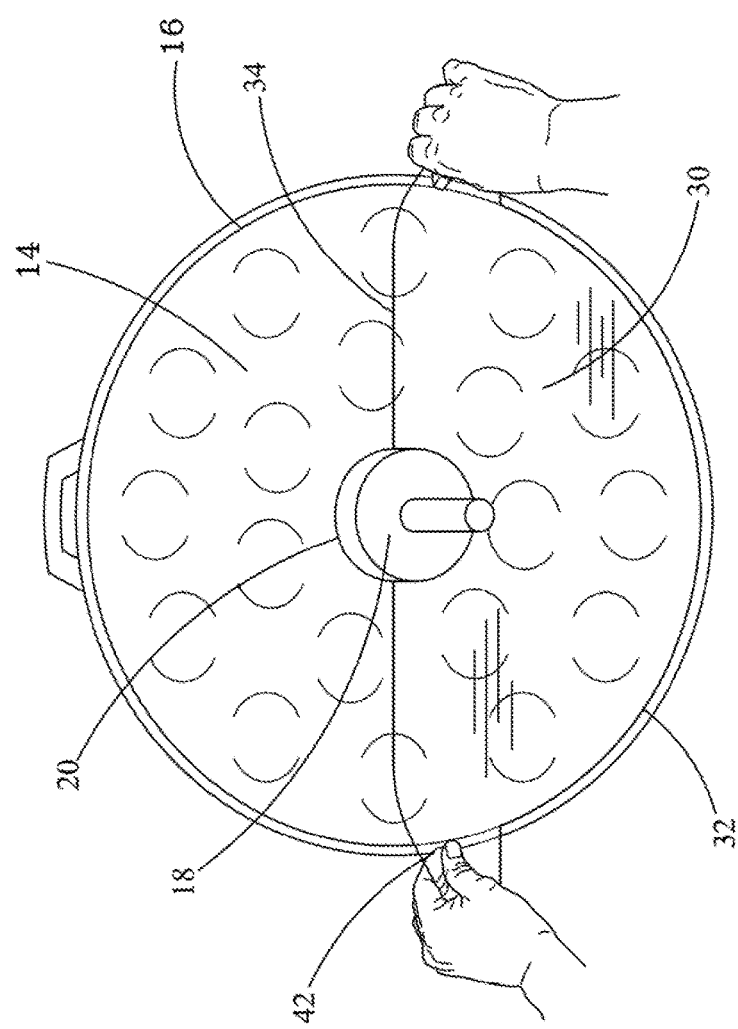
FIG. 11 is a view similar to FIG. 10 illustrating the bonding of the first optically transparent film to the surgical room light.

FIG. 10 shows the surgical light room 12, and the hands 130 of the installer positioning the first optically transparent film 30 to the surgical light room light surface 14. FIG. 10 also shows how the first grasping tabs 64 are used to aid in the positioning the first optically transparent film 30 to the surgical light room light surface 14. The first grasping tabs 64 and the second grasping tabs 84, shown in FIG. 9, are typically manufactured as square in shape, but in some instances another shape may prove beneficial. FIG. 11 is similar to FIG. 10. In FIG. 11, however, it shows the first optically transparent film 30 is being bonded to the surgical light room light surface 14.

Figure 12:
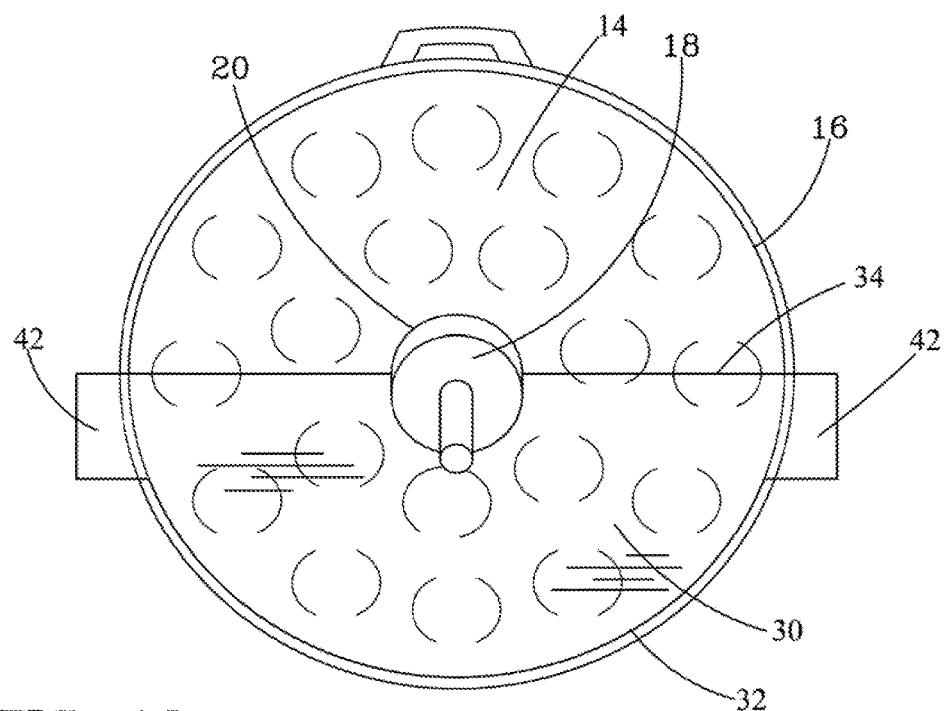
FIG. 12 is a view similar to FIG. 11 illustrating the first optically transparent film bonded to the surgical room light.

FIG. 12 shows the first optically transparent film 30 actually bonded to the surgical light room light surface 14. FIG. 12 also shows the first partial circular notch 36 and the handle circumferential edge 20 abutting for creating a first contiguous abutment 22. The second partial circular notch 76 and the handle circumferential edge 20 abutting for creating a second contiguous abutment 24.

Figure 13:
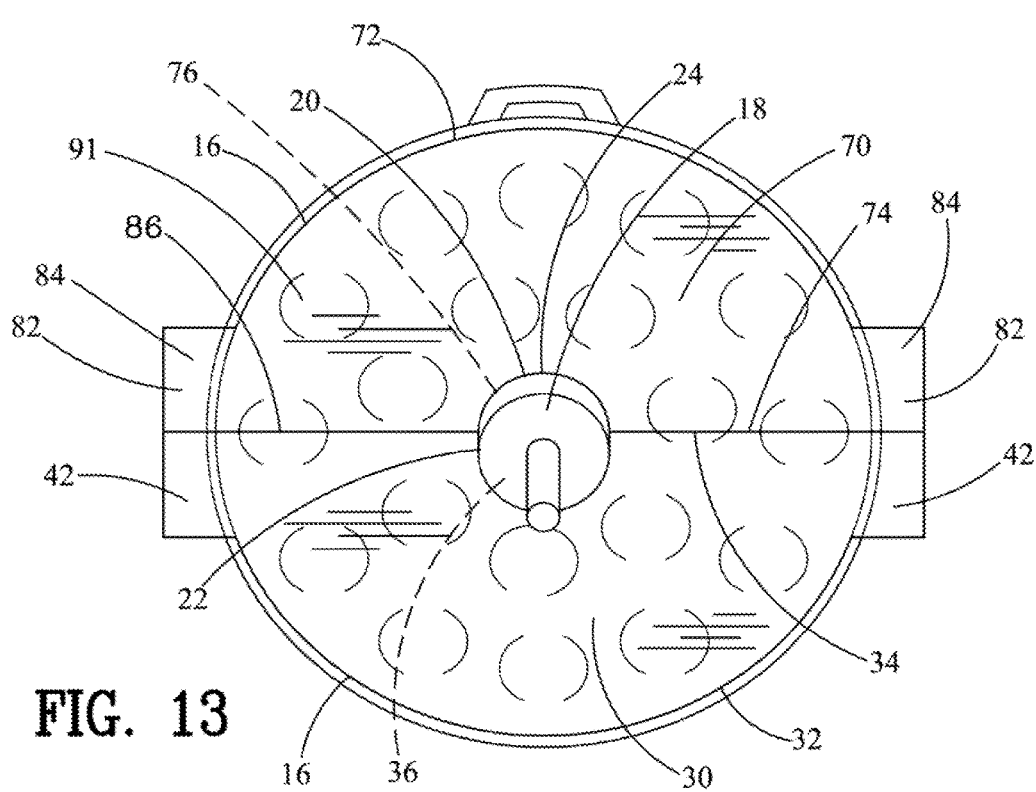
FIG. 13 is a view similar to FIG. 12 illustrating the first and the second optically transparent film bonded to the surgical light.

FIG. 13 illustrates the first optically transparent film 30 and the second optically transparent film 70 actually bonded to the surgical light room light surface 14. It is also shown that the first film edge 34 and the second film edge 74 are abutting for defining a contiguous joint 86 for covering the light surface 14. The first optically transparent film 30 and the second optically transparent film 70 create an annular film 91 that covers the light surface 14 of the surgical room light 12 which containing the microorganisms 126 between the light surface 14 and the annular film 91.

Often the top of the surgical room light 12 contains microorganisms, that may fall from the light and onto or into the patient. FIG. 14 illustrates the first film circumferential edge 32 can extend beyond the surgical room light circumferential edge 16 and define a first cantilever film portion 120. FIG. 14 also shows that in some cases the first film tabs 42 are affixed to and extending outwardly from opposed edges of the first film circumferential edge 32 and maybe parallel with the first film edge 34.

FIG. 15 is a side view of the overhead light shield 10. FIG. 16 shows the side view of the overhead light shield 10 by enlarging a section of FIG. 15. FIG. 16 shows the first optically transparent film 30 having a first upper film side 38 and a first lower film side 39 and the first adhesive layer 40 being affixed to the first lower film side 39. FIG. 16 also shows the first peel-away film 50 having a first upper peel-away film side 56 and a first lower peel-away film side 58. The first upper peel-away film side 56 is removably affixed to the first adhesive layer 40 for protecting the first adhesive layer 40 between the first optically transparent film 30 and the first peel-away film 50.

FIG. 17 shows the second optically transparent film 70. The second film circumferential edge 72 may extend beyond the surgical room light circumferential edge 16 and define a second cantilever film portion 122. The first cantilever film portion 120 and the second cantilever film portion 122 define an exterior annular ring 124 for trapping microorganisms 126 descending from above the light surface 14. The second film tabs 82, shown in FIG. 6, may also be affixed to and extend outwardly from opposed edges of the second film circumferential edge 72 and maybe parallel with the second film edge 74. In some cases the second film tabs 82 are affixed to and extending outwardly from opposed edges of the second film circumferential edge 72 and maybe parallel with the second film edge 74. Similarly, as shown in FIG. 4, the first peel-away tabs 60 are affixed to and extend outwardly from opposed edges of first peel-away film circumferential edge 52 and maybe parallel with first peel-away film edge 54.

Figure 18:
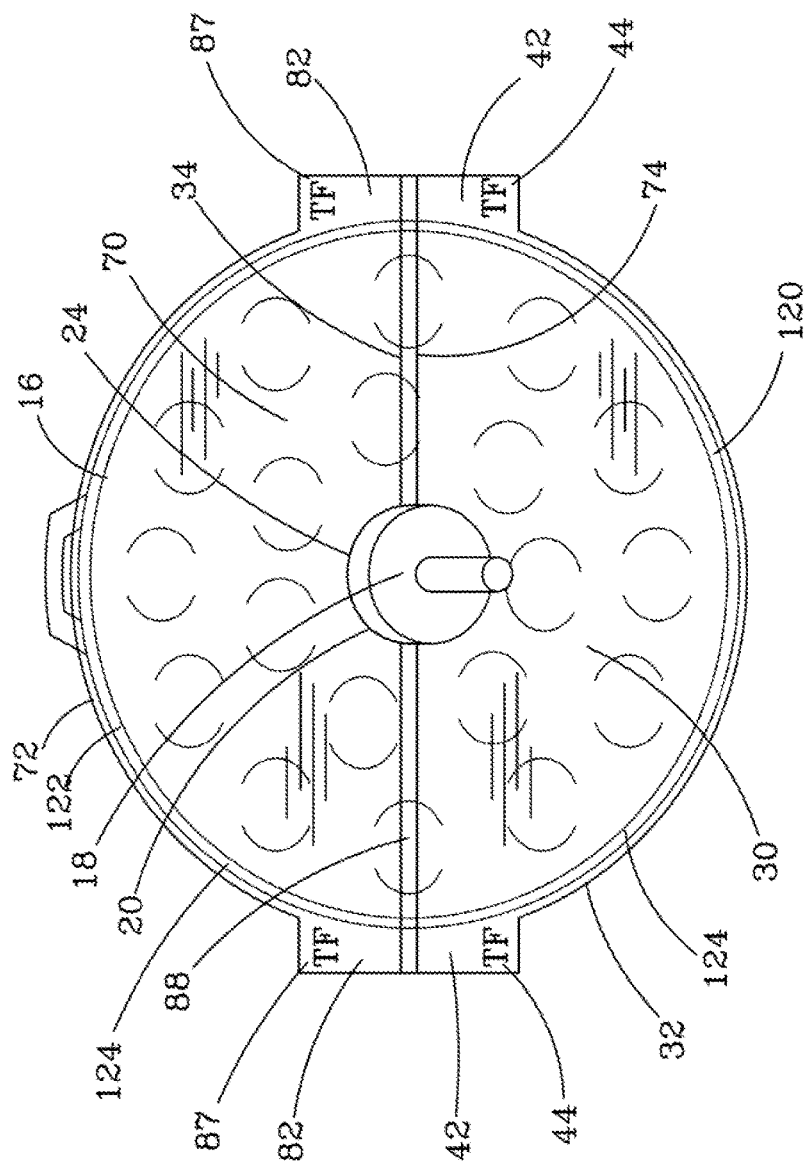
FIG. 18 is a view of the first optically transparent film and the second optically transparent film bonded to the surgical room light and illustrating first film edge and the second film edge overlapping.

FIG. 18 shows that the first film edge 34 and the second film edge 74 may overlap for defining a layered contiguous joint 88 for covering the light surface 14.

Figure 19:
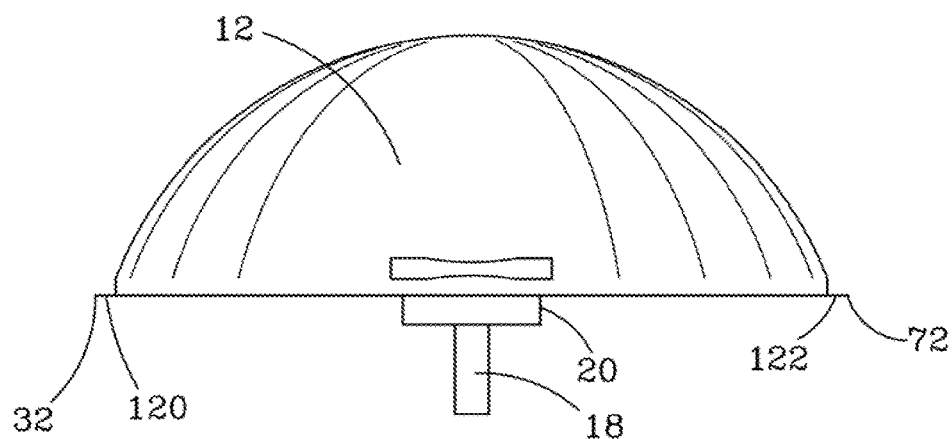
FIG. 19 is a side view of a surgical room light and illustrating first film circumferential edge overlapping the surgical room light circumferential edge.

FIG. 19 shows a side view of the surgical room light 12 and illustrates the first cantilever film portion 120 and the second cantilever film portion 122 overhanging the surgical room light 12 for catching any microorganisms 126 that may fall from above the surgical room light 12.

Figure 20:
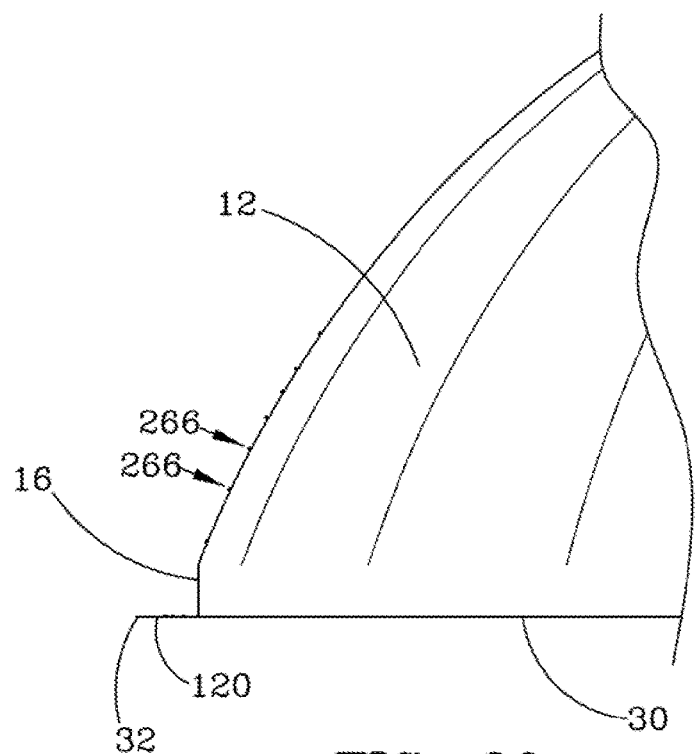
FIG. 20 is an enlarged portion of FIG. 19 illustrating microorganisms falling from above the surgical room light and becoming trapped by the overlapping first film circumferential edge.
Figure 21:
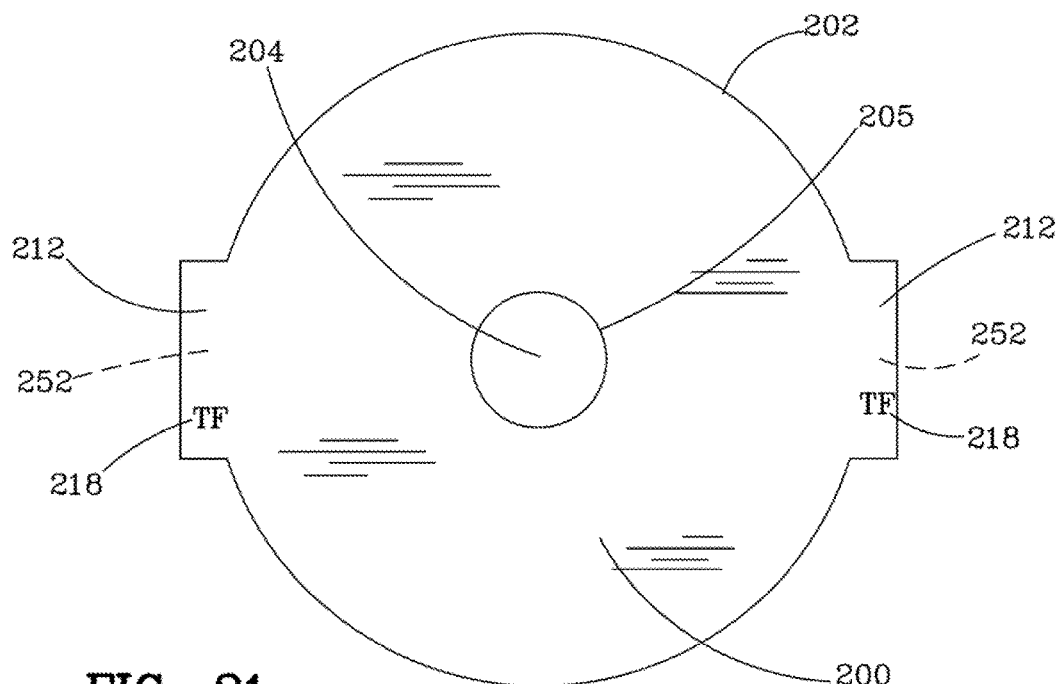
FIG. 21 is a top view of the second embodiment overhead light shield incorporating the present invention where the overhead light shield is a single piece.
Figure 22:
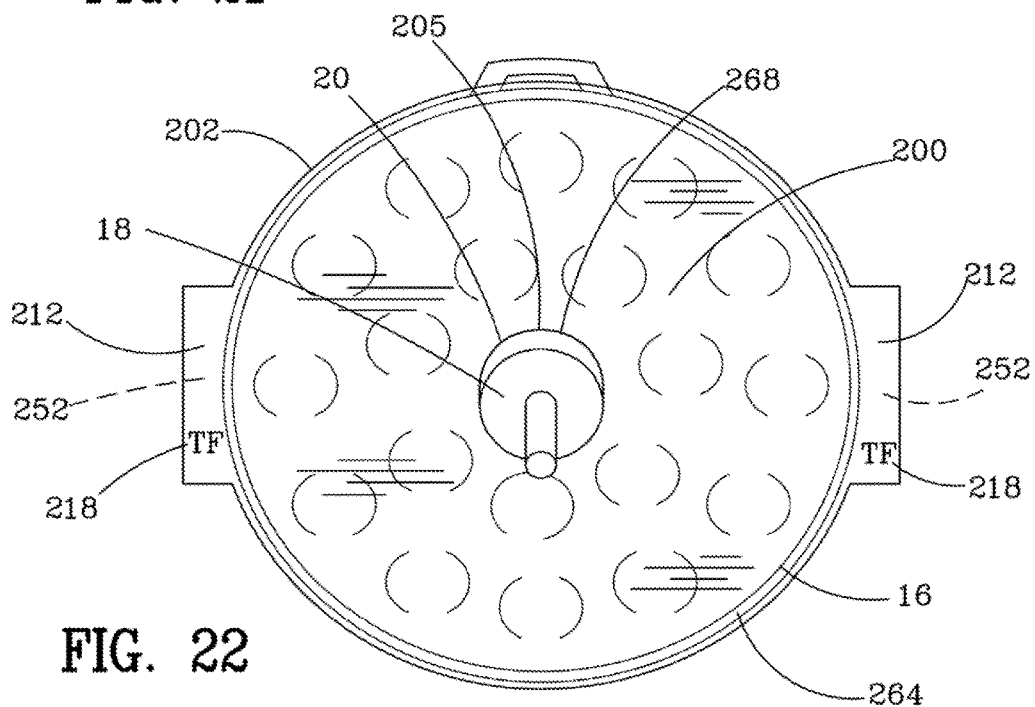
FIG. 22 is a view of the second embodiment bonded to the surgical room light.

FIG. 20 is a enlarged section of FIG. 19 to better show the microorganisms 126 falling from above and around the surgical room light 12. It is important to note that the microorganisms 126 have been exaggerated for better viewing.

In another embodiment of the invention, the optically transparent film 200 is one continuous piece that covers the entire light surface 14 of the surgical room light 12. Here the optically transparent film 200 is circular and defines a film circumferential edge 202. An optically transparent film circular aperture 204 is defined in the optically transparent film 200 and is coaxial with the film circumferential edge 202. The optically transparent film 200 has an upper film side 206 and a lower film side 208. An adhesive layer 210 is affixed to the lower film side 208. A plurality of film tabs 212 are affixed to and extend outwardly from the film circumferential edge 202. A peel-away film 240 is circular and defines a peel-away film circumferential edge 242. A peel-away film circular aperture 244 is defined in the peel-away film 240 and is coaxial with the peel-away film circumferential edge 242. The peel-away film has an upper peel-away film side 246 and a lower peel-away film side 248. The upper peel-away film side 246 is removably affixed to the adhesive layer 210 for protecting the adhesive layer 210 between the optically transparent film 200 and the peel-away film 240. A plurality of peel-away tabs 250 are affixed to and extend outwardly from the peel-away film circumferential edge 242. The plurality of peel-away tabs 250 and the plurality of film tabs 212 define a plurality of disjoining tabs 260 for separating the peel-away film 240 from the adhesive layer 210. The plurality of film tabs 212 define a plurality of grasping tabs 214 for positioning the optically transparent film 200 adjacent to the surgical room light 12. The adhesive layer 210 defines a coupling joint 216 for bonding the optically transparent film 200 with the surgical room light 12. The film circumferential edge 202 extends beyond the surgical room light circumferential edge 16 for defining a cantilever film portion 262. The cantilever film portion 262 defines an exterior annular ring 264 for trapping microorganisms 266 descending from above the light surface 14. The peel-away film 240 may be a thinner film than the optically transparent film 200 for easier identification. The film tabs 212 may include a film tabs symbol 218 for identifying the optically transparent film 200. The peel-away film tabs may have a peel-away film tabs symbol 252 for identifying the peel-away film 240. The film tabs 212 are affixed to and extend outwardly from opposed edges of the film circumferential edge 202. The peel-away tabs 250 are affixed to and extend outwardly from opposed edges of the peel-away film circumferential edge 242. The circular aperture 204 and the handle circumferential edge 20 abut for creating a contiguous abutment 268.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An overhead light shield for covering a surgical room light wherein the surgical room light has a light surface, a circumferential edge and a center handle, the center handle having a handle circumferential edge, overhead light shield comprising;
    a first optically transparent film being partially circle defining a first film circumferential edge and a first film edge;
    a first partial circular notch defined in said first optically transparent film interposed in said first film edge;
    said first optically transparent film having a first upper film side and a first lower film side;
    a first adhesive layer affixed to said first lower film side;
    a plurality of first film tabs affixed to and extending outwardly from said first film circumferential edge;
    a first peel-away film being partially circle defining a first peel-away film circumferential edge and a first peel-away film edge;
    said first peel-away film having a first upper peel-away film side and a first lower peel-away film side;
    said first upper peel-away film side removably affixed to said first adhesive layer for protecting said first adhesive layer between said first optically transparent film and said first peel-away film;
    a plurality of first peel-away tabs affixed to and extending outwardly from said first peel-away film circumferential edge;
    said plurality of first peel-away tabs and said plurality of first film tabs defining a plurality of first disjoining tabs for separating said first peel-away film from said first adhesive layer,
    said plurality of first film tabs defining a plurality of first grasping tabs for positioning said first optically transparent film adjacent to the surgical room light;
    said first adhesive layer defining a first coupling joint for bonding said first optically transparent film with said surgical room light;
    a second optically transparent film being partially circle defining a second film circumferential edge and a second film edge;
    a second partial circular notch defined in said second optically transparent film interposed in said second film edge;
    said second optically transparent film having a second upper film side and a second lower film side;
    a second adhesive layer affixed to said second lower film side;
    a plurality of second film tabs affixed to and extending outwardly from said second film circumferential edge;
    a second peel-away film being partially circle defining a second peel-away film circumferential edge and a second peel-away film edge;
    said second peel-away film having a second upper peel-away film side and a second lower peel-away film side;
    said second upper peel-away film side removably affixed to said second adhesive layer for protecting said second adhesive layer between said second optically transparent film and said second peel-away film;
    a plurality of second peel-away tabs affixed to and extending outwardly from said second peel-away film circumferential edge;
    said plurality of second peel-away tabs and said plurality of second film tabs defining a plurality of second disjoining tabs for separating said second peel-away film from said second adhesive layer;
    said plurality of second film tabs defining a plurality of second grasping tabs for positioning said second optically transparent film adjacent to the surgical room light; and
    said second adhesive layer defining a second coupling joint for bonding said second optically transparent film with said surgical room light.

2. An overhead light shield for covering a surgical room light as set forth in claim 1, wherein said first grasping tabs and said second grasping tabs are square.

3. An overhead light shield used to cover a surgical room light as set forth in claim 1, wherein said first film circumferential edge extends beyond the surgical room light circumferential edge for defining a first cantilever film portion;
    said second film circumferential edge extends beyond the surgical room light circumferential edge for defining a second cantilever film portion; and
    said first cantilever film portion and said second cantilever film portion defining an exterior annular ring for trapping microorganisms descending from above the light surface.

4. An overhead light shield used to cover a surgical room light as set forth in claim 1, wherein said first peel-away film being a thinner film than said first optically transparent film for easier identification; and
    said second peel-away film being a thinner film than said second optically transparent film for easier identification.

5. An overhead light shield used to cover a surgical room light as set forth in claim 1, wherein said first film tabs having a first film tabs symbol for identifying said first optically transparent film;
    said second film tabs having a second film tabs symbol for identifying said second optically transparent film;

said first peel-away film tabs having a first peel-away film tabs symbol for identifying said first peel-away film; and said second peel-away film tabs having a second peel-away film tabs symbol for identifying said second peel-away film.

6. An overhead light shield used to cover a surgical room light as set forth in claim 1, wherein said first film tabs affixed to and extending outwardly from opposed edges of said first film circumferential edge;

said second film tabs affixed to and extending outwardly from opposed edges of said second film circumferential edge;

said first peel-away tabs affixed to and extending outwardly from opposed edges of first peel-away film circumferential edge; and said second peel-away tabs affixed to and extending outwardly from opposed edges of second peel-away film circumferential edge.

7. An overhead light shield used to cover a surgical room light as set forth in claim 1, wherein said first film tabs affixed to and extending outwardly from opposed edges of said first film circumferential edge and parallel with said first film edge;

said second film tabs affixed to and extending outwardly from opposed edges of said second film circumferential edge and parallel with said second film edge;

said first peel-away tabs affixed to and extending outwardly from opposed edges of first peel-away film circumferential edge and parallel with first peel-away film edge; and said second peel-away tabs affixed to and extending outwardly from opposed edges of second peel-away film circumferential edge and parallel with second peel-away film edge.

8. An overhead light shield used to cover a surgical room light as set forth in claim 1, wherein said first film edge and said second film edge abutting for defining a contiguous joint for covering the light surface.

9. An overhead light shield used to cover a surgical room light as set forth in claim 1, wherein said first film edge and said second film edge overlapping for defining a layered contiguous joint for covering the light surface.

10. An overhead light shield used to cover a surgical room light as set forth in claim 1, wherein said first partial circular notch and the handle circumferential edge abutting for creating a first contiguous abutment; and said second partial circular notch and the handle circumferential edge abutting for creating a second contiguous abutment.

11. An overhead light shield for covering a surgical room light wherein the surgical room light has a light surface having microorganisms in contact with the light surface, a circumferential edge and a center handle, the center handle having a handle circumferential edge, overhead light shield comprising;

a first optically transparent film being partially circle defining a first film circumferential edge and a first film edge;

a first partial circular notch defined in said first optically transparent film interposed in said first film edge;

said first optically transparent film having a first upper film side and a first lower film side;

a first adhesive layer affixed to said first lower film side;

a plurality of first film tabs affixed to and extending outwardly from said first film circumferential edge;

a first peel-away film being partially circle defining a first peel-away film circumferential edge and a first peel-away film edge;

said first peel-away film having a first upper peel-away film side and a first lower peel-away film side;

said first upper peel-away film side removably affixed to said first adhesive layer for protecting said first adhesive layer between said first optically transparent film and said first peel-away film;

a plurality of first peel-away tabs affixed to and extending outwardly from said first peel-away film circumferential edge;

said plurality of first peel-away tabs and said plurality of first film tabs defining a plurality of first disjoining tabs for separating said first peel-away film from said first adhesive layer;

said plurality of first film tabs defining a plurality of first grasping tabs for positioning said first optically transparent film adjacent to the surgical room light;

said first adhesive layer defining a first coupling joint for bonding said first optically transparent film with said surgical room light;

a second optically transparent film being partially circle defining a second film circumferential edge and a second film edge;

a second partial circular notch defined in said second optically transparent film interposed in said second film edge;

said second optically transparent film having a second upper film side and a second lower film side;

a second adhesive layer affixed to said second lower film side;

a plurality of second film tabs affixed to and extending outwardly from said second film circumferential edge;

a second peel-away film being partially circle defining a second peel-away film circumferential edge and a second peel-away film edge;

said second peel-away film having a second upper peel-away film side and a second lower peel-away film side;

said second upper peel-away film side removably affixed to said second adhesive layer for protecting said second adhesive layer between said second optically transparent film and said second peel-away film;

a plurality of second peel-away tabs affixed to and extending outwardly from said second peel-away film circumferential edge;

said plurality of second peel-away tabs and said plurality of second film tabs defining a plurality of second disjoining tabs for separating said second peel-away film from said second adhesive layer;

said plurality of second film tabs defining a plurality of second grasping tabs for positioning said second optically transparent film adjacent to the surgical mom light;

said second adhesive layer defining a second coupling joint for bonding said second optically transparent film with said surgical room light;

said first optically transparent film and said second optically transparent film defining an annular film for covering the light surface of the surgical room light for containing microorganisms between the light surface and said annular film;

said first partial circular notch and the handle circumferential edge abutting for creating a first contiguous abutment;

said second partial circular notch and the handle circumferential edge abutting for creating a second contiguous abutment;

said first film circumferential edge extends beyond the surgical room light circumferential edge for defining a first cantilever film portion;

said second film circumferential edge extends beyond the surgical room light circumferential edge for defining a second cantilever film portion; and said first cantilever film portion and said second cantilever film portion defining an exterior surface, annular ring for trapping microorganisms descending from above the light surface, said first film tabs affixed to and extending outwardly from opposed edges of said first film circumferential edge;

said second film tabs affixed to and extending outwardly from opposed edges of said second film circumferential edge;

said first peel-away tabs affixed to and extending outwardly from opposed edges of first peel-away film circumferential edge;

said second peel-away tabs affixed to and extending outwardly from opposed edges of second peel-away film circumferential edge; and said first film edge and said second film edge abutting for defining a contiguous joint for covering the light surface.

12. An overhead light shield for covering a surgical room light as set forth in claim 11, wherein said first grasping tabs and said second grasping tabs are square.

13. An overhead light shield used to cover a surgical room light as set forth in claim 11, wherein said first peel-away film being a thinner film than said first optically transparent film for easier identification; and said second peel-away film being a thinner film than said second optically transparent film for easier identification.

14. An overhead light shield used to cover a surgical room light as set forth in claim 11, wherein said first film tabs having a first film tabs symbol for identifying said first optically transparent film;

said second film tabs having a second film tabs symbol for identifying said second optically transparent film;

said first peel-away film tabs having a first peel-away film tabs symbol for identifying said first peel-away film; and said second peel-away film tabs having a second peel-away film tabs symbol for identifying said second peel-away film.

15. An overhead light shield used to cover a surgical room light as set forth in claim 11, wherein said first film tabs affixed to and extending outwardly from opposed edges of said first film circumferential edge and parallel with said first film edge;

said second film tabs affixed to and extending outwardly from opposed edges of said second film circumferential edge and parallel with said second film edge;

said first peel-away tabs affixed to and extending outwardly from opposed edges of first peel-away film circumferential edge and parallel with first peel-away film edge; and said second peel-away tabs affixed to and extending outwardly from opposed edges of second peel-away film circumferential edge and parallel with second peel-away film edge.

16. An overhead light shield used to cover a surgical room light as set forth in claim 11, wherein said first film edge and said second film edge overlapping for defining a layered contiguous joint for covering the light surface.

17. An overhead light shield for covering a surgical room light wherein the surgical room light has a light surface, a circumferential edge and a center handle, the center handle having a handle circumferential edge, overhead light shield comprising;

an optically transparent film being circular defining a film circumferential edge;

an optically transparent film circular aperture defined in said optically transparent film coaxial with said film circumferential edge;

said optically transparent film having a upper film side and a lower film side;

an adhesive layer affixed to said lower film side;

a plurality of film tabs affixed to and extending outwardly from said film circumferential edge;

a peel-away film being circular defining a peel-away film circumferential edge;

a peel-away film circular aperture defined in said peel-away film coaxial with said peel-away film circumferential edge;

said peel-away film having an upper peel-away film side and a lower peel-away film side;

said upper peel-away film side removably affixed to said adhesive layer for protecting said adhesive layer between said optically transparent film and said peel-away film;

a plurality of peel-away tabs affixed to and extending outwardly from said peel-away film circumferential edge;

said plurality of peel-away tabs and said plurality of film tabs defining a plurality of disjoining tabs for separating said peel-away film from said adhesive layer;

said plurality of film tabs defining a plurality of grasping tabs for positioning said optically transparent film adjacent to the surgical room light;

said adhesive layer defining a coupling joint for bonding said optically transparent film with said surgical room light.

18. An overhead light shield used to cover a surgical room light as set forth in claim 17, wherein said film circumferential edge extends beyond the surgical room light circumferential edge for defining a cantilever film portion;

said cantilever film portion defining an exterior annular ring for trapping microorganisms descending from above the light surface.

19. An overhead light shield used to cover a surgical room light as set forth in claim 17, wherein said peel-away film being a thinner film than said optically transparent film for easier identification.

20. An overhead light shield used to cover a surgical room light as set forth in claim 17, wherein said film tabs having a film tabs symbol for identifying said optically transparent film;

said peel-away film tabs having a peel-away film tabs symbol for identifying said peel-away film.

21. An overhead light shield used to cover a surgical room light as set forth in claim 17, wherein said film tabs affixed to and extending outwardly from opposed edges of said film circumferential edge; and said peel-away tabs affixed to and extending outwardly from opposed edges of peel-away film circumferential edge.

22. An overhead light shield used to cover a surgical room light as set forth in claim 17, wherein said circular aperture and the handle circumferential edge abutting for creating a contiguous abutment.

* * * * *